US007056521B2

(12) United States Patent
Barchfeld et al.

(10) Patent No.: US 7,056,521 B2
(45) Date of Patent: Jun. 6, 2006

(54) DETOXIFIED MUTANTS OF BACTERIAL ADP-RIBOSYLATING TOXINS AS PARENTERAL ADJUVANTS

(75) Inventors: Gail Barchfeld, Hayward, CA (US); Giuseppe Del Giudice, Siena (IT); Rino Rappuoli, Siena (IT)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/927,561

(22) Filed: Aug. 26, 2004

(65) Prior Publication Data

US 2005/0106180 A1 May 19, 2005

Related U.S. Application Data

(63) Continuation of application No. 09/044,696, filed on Mar. 18, 1998, now Pat. No. 6,818,222.

(60) Provisional application No. 60/041,227, filed on Mar. 21, 1997.

(51) Int. Cl.
*A61K 39/02* (2006.01)
*A61K 45/00* (2006.01)
*A61K 39/10* (2006.01)
*A61K 39/295* (2006.01)

(52) U.S. Cl. .............. 424/236.1; 424/234.1; 424/241.1; 424/282.1; 424/202.1; 424/209.1; 424/217.1; 424/278.1; 424/240.1; 424/254.1; 424/257.1; 424/261.1; 514/2

(58) Field of Classification Search .............. 424/236.1, 424/234.1, 282.1, 202.1, 209.1, 278.1, 217.1, 424/240.1, 241.1, 254.1, 261.1, 257.1; 514/2, 514/837, 867; 530/350, 825
See application file for complete search history.

(56) References Cited

U.S. PATENT DOCUMENTS 5,182,109 A 1/1993 Tamura et al.
6,818,222 B1 * 11/2004 Barchfeld et al. ....... 424/236.1

FOREIGN PATENT DOCUMENTS

| EP | 0 145 486 A2 | 6/1985 |
|---|---|---|
| EP | 0396964 | 11/1990 |
| EP | 0462534 | 12/1991 |
| WO | WO 92/19265 | 11/1992 |
| WO | WO 93/13202 | 7/1993 |
| WO | WO 95/17211 | 7/1993 |
| WO | WO 95/09649 | 4/1995 |
| WO | WO 95/34323 | 12/1995 |
| WO | WO 96/06627 | 3/1996 |
| WO | WO 97/02348 | 1/1997 |
| WO | WO 99/58145 | 11/1999 |
| WO | WO 00/18434 | 4/2000 |

OTHER PUBLICATIONS

Agren, et al., "Genetically Engineered Nontoxic Vaccine Adjuvant That Combines B Cell Targeting with Immunomodulation by Cholera Toxin A1 Subunit," *J. Immunol.* 158:3936-3946 (1997).
Akhiani, et al., "Effect of Cholera Toxin on Vaccine-Induced Immunity and Infection in Murine Schistosomiasis Mansoni," *Infection and Immunity* 61(11): 4919-4924 (1993).
Bowen, et al., "Cholera Toxin Acts as a Potent Adjuvant for the Induction of Cytotoxic T-Lymphocyte Responses With Non-Replicating Antigens," *Immunology* 81:338-342 (1994).
Burnette, et al., "Site-Specific Mutagenisis of the Catalytic Subunit of Cholera Toxin: Substituting Lysine for Arginine 7 Causes Loss of Activity," *Infection and Immunity* 59(11):4266-4270 (1991).
Clements, et al., "Adjuvent Activity of *Escherichia coli* Heat Labile Enterotoxin and Effect on the Induction of Oral Tolerance in Mice to Unrelated Protein Antigens," *Vaccine* 6:269-277.
Di Tommaso, et al., "Induction of Antigen-Specific Antibodies in Vaginal Secretions by Using a Nontoxic Mutant of Heat-Labile Enterotoxin as a Mucosal Adjuvant," *Infection and Immunity* 64(3): 974-979 (1996).
Douce, et al., "Mutants of *Escherichia coli* Heat Labile Toxin Lacking ADP-Ribosyltransferase Activity Act as Nontoxic, Mucosal Adjuvants," *Proc. Natl. Acad. Sci. USA* 92:1644-1648 (1995).
Douce, et al., "Intranasal Immunogenecity and Adjuvanticity of Site-Directed Mutant Derivatives of Cholera Toxin," *Infection and Immunity* 65(7): 2821-2828 (1997).
Elson, et al., "Cholera Toxin as a Mucosal Adjuvant," *Mucosal Vaccines* 4:59-72 (1996).
Elson, et al., "Cholera Toxin and its Subunits as Potential Oral Adjuvants," *Curr. Top. Microbiol. Immonol.* 146:29-33 (1989).
Elson, et al., "A Lavage Technique Allowing Repeated Measurement of IgA Antibody in Mouse Intestinal Secretions," *Journal of Immunological Methods* 67:101-108 (1984).
Elson, et al., "Generalized Systematic and Mucosal Immunity in Mice After Mucosal Stimulation with Cholera Toxin," *The Journal of Immunology* 132(6): 2736-2741 (1984).
Elson, et al., "Ir Gene Control of the Murine Secretory IgA Response to Cholera Toxin," *Eur. J. Immonol.* 17:425-428 (1987).

(Continued)

Primary Examiner—S. Devi
(74) *Attorney, Agent, or Firm*—Rebecca M. Hale; Dahna S. Pasternak; Alisa A. Harbin (57) ABSTRACT

The present invention provides parenteral adjuvants comprising detoxified mutants of bacterial ADP-ribosylating toxins, particularly those from pertussis (PT), cholera (CT), and heat-labile *E. coli* (LT).

19 Claims, 3 Drawing Sheets

OTHER PUBLICATIONS

Elson, et al., "Cholera Toxin Feeding Did Not Induce Oral Tolerance in Mice and Abrogated Oral Tolerance to an Unrelated Protein Antigen," *The Journal of Immunology* 133(6): 2829-2897 (1984).

Fontana, et al., "Construction of Nontoxic Derivatives of Cholera Toxin and Characterization of the Immunological Response Against the A Subunit," *Infection and Immunity* 64(12): 5434-5438 (1996).

Gizurarson, et al., "The Effect of Cholera Toxin and Cholera Toxin B Subunit on the Nasal Mucosal Membrane," *Vaccine* 9:825-832 (1991).

Glenn, et al., "Skin Immunization Made Possible by Cholera Toxin," *NATURE* 391:851 (1998).

Harford, et al., "Inactivation of the *Escherichia coli* Heat-Labile Enterotoxin by In Vitro Mutagenesis of the A-Subunit Gene," *Eur. J. Biochem.* 183:311-316 (1989).

Hirabayashi, et al., "Involvement of Antigen-Presenting Cells in the Enhancement of the In Vitro Antibody Responses by Cholera Toxin B Subunit," *Immunology* 75:493-498 (1992).

Hirabayashi, et al., "Comparison of Intranasal Inoculation of Influenza HA Vaccine Combined With Cholera Toxin B Subunit With Oral or Parenteral Vaccination," *Vaccine* 8:243-248 (1990).

Hirabayashi, et al., "H-2-Unrestricted Adjuvant Effect of Cholera Toxin B Subunit on Murine Antibody Responses to Influenza Virus Haemagglutinin," *Immunology* 72:329-335 (1991).

Holmgren, et al., "An Oral B Subunit: Whole Cell Vaccine Against Cholera," *Vaccine* 10(13): 911-914 (1992).

Holmgren, et al., "Cholera Toxin and Cholera B Subunit as Oral-Mucosal Adjuvant and Antigen Vector Systems," *Vaccine* 11:1179-1183 (1993).

Jackson, et al., "Optimizing Oral Vaccines: Induction of Systematic and Mucosal B-Cell and Antibody Responses to Tetanus Toxoid by Use of Cholera Toxin as an Adjuvant," *Infection and Immunity* 61(10): 4272-4279 (1993).

Kikuta, et al., "Cross-Protection Against Influenza B Type Virus Infection by Intranasal Inoculation of the HA Vaccines Combined with Cholera Toxin B Subunit," *Vaccine* 8:595-599 (1990).

Lycke, et al., "The Adjuvant Effect of *Vibrio Cholera* and *Escherichia coli* Heat Labile Enterotoxins is Linked to Their ADP- Ribosyltransferase Activity," *Eur. J. Immunol.* 22: 2277-2281 (1992).

Lyke, et al., "Strong Adjuvant Properties of Cholera Toxin on Gut Mucosal Immune Responses to Orally Presented Antigens," *Immunology* 59:301-308 (1986).

Magagnoli, et al., "Mutations in the A Subunit Affect Yield, Stability, and Protease Sensitivity on Nontoxic Derivatives of Heat-Labile Enterotoxin," *Infection and Immunity* 64(12): 5434-5438 (1996).

Nasher, et al., "Potent Immunologenicity of the B Subunits of *Escherichia coli* Heat-Labile Enterotoxin: Receptor Binding is Essential and Induces Differential Modulation of Lymphocyte Subsets," *Proc. Natl. Acad. Sci. USA* 93:226-230 (1996).

Partidos, et al., "The Adjuvant Effect of a Non-Toxic Mutant of Heat-Labile Enterotoxin of *Escherichia coli* for the Induction of Measles Virus-Specific CTL Responses After Intranasal Co-Immunization With a Synthetic Peptide," *Immunology* 89:483-487 (1996).

Pierce, "The Role of Antigen Form and Function in the Primary and Secondary Intestinal Immune Responses to Cholera Toxin and Toxoid in Rats," *J. Exp. Med.* 148:195-206 (1978).

Pierce, et al., "Cellular Kinetics of the Intestinal Immune Response to Cholera Toxoid in Rats," *J. Exp. Med.* 142:1550-1563 (1975).

Pizza, et al., "Probing the Structure-Activity Relationship of *Escherichia coli* LT-A by Site-Directed Mutagenesis," *Molecular Micobiology* 14(1): 51-60 (1994).

Rollwagen, et al., "Killed *Campylobacter* Elicits Immune Response and Protection When Administered with an Oral Adjuvant," *Vaccine* 11(13): 1316-1320 (1993).

Snider, "The Mucosal Adjuvant Activities of ADP-Ribosylating Bacterial Enterotoxins," *Critical Review in Immunology* 15(3&4): 317-348 (1995).

Tamura, et al., "Cross-Protection Against Influenza Virus Infection Afforded By a Trivalent Inactivated Vaccines Inoculated Intranasally with Cholera Toxin B Subunit," *The Journal of Immunology* 149(3): 981-988 (1992).

Tamura, et al., "Protection Against Influenza Virus Infection by a Two-Dose Regimen of Nasal Vaccination Using Vaccines Combined with Cholera Toxin B Subunit," *Vaccine* 7:314-320 (1989).

Tamura, et al., "Enhancement of Protective Antibody Responses by Cholera Toxin B Subunit Inoculated Intranasally With Influenza Vaccine," *Vaccine* 7:257-262 (1989).

Tamura, et al., "Protection Against Influenza Virus Infection by Vaccine Inoculated Intranasally With Cholera Toxin B Subunit," *Vaccine* 6:409-413 (1988).

Tamura, et al., "Effectiveness of Cholera Toxin B Subunit as an Adjuvant for Nasal Influenza Vaccination Despite Pre-Existing Immunity to CTB," *Vaccine* 7:503-505 (1989).

Tsuji, et al., "A Single Amino Acid Substitution in the A Subunit of *Escherichia coli* Enterotoxin Results in a Loss of its Toxic Activity," *The Journal of Biological Chemistry* 265(36): 22520-22525 (1990).

Van Den Akker, et al., "The Arg7Lys Mutant of Heat-Labile Enterotoxin Exhibits Great Flexibility of Active Site Loop 47-56 of the A Subunit," *Biochemistry* 34:10996-11004 (1995).

Van Der Heijden, et al., "Manipulation of Intestinal Immune Responses Against Ovalbumin by Cholera Toxin and its B Subunit in Mice," *Immunology* 72:89-93 (1991).

Wilson, et al., "Adjuvant Action of Cholera Toxin on the Mucosal Immune Response to Soluble Proteins, Differences Between Mouse Strains and Protein Antigens," *Scand. J. Immunol.* 29:739-745 (1989).

Wilson, et al., "Adjuvant Action of Cholera Toxin and Pertussis Toxin in the Induction of IgA Antibody Response to Orally Administered Antigen," *Vaccine* 11(2): 113-115 (1993).

Burnette, "The Advent of Recombinant Pertussis Vaccines." *Biotechnol.* 8:1002-1005 (1990).

Burnette, *Vaccine Research & Developments* Marcel Dekker Inc., New York, New York (1992).

Communication to EPO Concerning Replacement Claims for Filing with the EPO in Application No. 99922284.7 (2003).

de Haan, et al., "Mutational Analysis of the Role of ADP-Ribosylation Activity in the Adjuvant Properties of the *Escherichia coli* Heat-Labile Enterotoxin Towards Intranasally Administered Keyhole Limpet Hemocyanin." *Eur. J. Immunol.* 28:1243-1250 (1998).

Del Guidice, et al., "Genetically Derived Toxoids for use as Vaccines and Adjuvants." *Vaccine* 17:S44-S52 (1999).

Dickinson & Clements, "Dissociation of *Escherichia coli* heat-labile enterotoxin adjuvanticity from ADP-ribosyltransferase activity", Infect.Immunity, 63:1617-1623 (1995).

EPO Communication pursuant to Article 96(2) EPC relating to Application EP No. 94928455.8-2116 (2001).

"Multicomponent Vaccine Development." *NIH Guide* vol. 22, No. 28 (1993).

Fontana et al., "Construction of Nontoxic Derivatives of Cholera Toxin and Characterization of the Immunological Response Against the A Subunit," *Infect. Immun.*, 63(6):2356-2360 (1995).

Grant et al., "Role of trypsin-like cleavage at arginine 192 in the enzymatic and cytotonic activities of *Escherichia coli* heat-labile enterotoxin", Infect. Immun., 62:4270-4278 (1994).

Green, Bruce, Curriculum Vitae.

Hagen, Michael, Curriculum Vitae.

Hagiwar, et al., Effectiveness and Safety of Mutant *Escherichia coli* Heat-Labile Enterotoxin (LT H44A) as an Adjuvant for Nasal Influenza Vaccine. *Vaccine* 19:2071-2079 (2001).

Hartman, et al., "Native and Mutant Forms of Cholera Toxin and Heat-Labile Enterotoxin Effectively Enhance Protective Efficacy of Live Attenuated and Heat-Killed Shigella Vaccines." *Infect. Immun.* 67:5841-5847 (1999).

Hazama, et al., "Intranasal Immunization Against Herpes Simplex Virus Infection by using a Recombinant Glycoprotein D Fused with Immunomodulating Proteins, the B Subunit of *Escherichia coli* Heat-Labile Enterotoxin and Interleukin-2." *Immunology* 78:643-649 (1993).

Hirst, et al., "Cholera Toxin and Related Enterotoxins as Potent Immune Modulators." *J. Appl. Microb. Symp. Suppl.* 48:26S-34S (1998).

Hirst, *The Comprehensive Sourcebook of Bacterial Protein Toxins*, Chapter 6, Academic Press, pp. 104-130, (1999).

Lobet et al.., "Effect of site-directed mutagenic alterations on ADP-ribosyltransferase activity of the A subunit of *Escherichia coli* heat-labile enterotoxin", Infect. Immun. 59:2870-2879 (1991).

Lycke, et al, "The Mechanism of Cholera Toxin Adjuvanticity." *Res. Immunol.* 198:504-520 (1997).

Martindale, *Royal Pharmaceutical Society of Britain* Pharmaceutical Press, London, England, pp. 1277-1304(1993).

Rappouli, et al., "Structure and Mucosal Adjuventicity of Cholera and *Escherichia Coli* Heat-Labile Enterotoxins." *Immunol. Today* 20:493-500 (1999).

Spangler, "Structure and Function of Cholera Toxin and The Related *Escherichia Coli* Heat-Labile Enterotoxin." *Microbiol. Rev.* 56:622-647 (1992).

Streatfield, et al. , "Intermolecular Interactions Between the A and B Subunits of Heat-Labile Enterotoxin from *Escherichia Coli* Promote Holotoxin Assembly and Stability In Vivo." *PNAS USA* 89:12140-12144 (1992).

*The Comprehensive Sourcebook of Bacterial Protein Toxins*, $2^{nd}$ Ed., Academic Press, pp. 696-697.

Tsuji, et al., "Relationship Between a Low Toxicity of the Mutant A Subunit of Enterotoxigenic *Escherichia Coli* Enterotoxin and its Strong Adjuvant Action." *Immunology* 90:176-182 (1997).

Verweij, et al.,Mucosal Immunoadjuvant Activity of Recombinant *Escherichia Coli* Heat-Labile Enterotoxin and its B Subunit: Induction of Systematic IgG and Secretory IgA Responses in Mice by Intranasal Immunization with Influenza Virus Surface Antigen. *Vaccine* 16:2069-2076 (1998).

Walker, et al., "Use of Heat-Labile Toxin Enterotoxigenic *Escherichia coli* to Facilitate Mucosal Immunization." *Vaccine Res.* 2:1-10 (1993).

Williams, Neil, Affidavit, Curriculum Vitae, and Annex 1.

Yamamoto, et al., "Mutants in the ADP-Ribosyltransferase Cleft of Cholera Toxin Lack Diarrheagenicity but Retain Adjuvanticity." *J. Exp. Med.* 185:1203-1210 (1997).

* cited by examiner

```
LT  AATGGCGACAGATTATACCGTGCTGACTCTAGACCCCCAGATGAAATAAAACGTTTCCGG
     N   G   D   R   L   Y   R   A   D   S   R   P   P   D   E   I   K   K   F   R      20
    ------------------------------------------------------------
     N   D   D   K   L   Y   R   A   D   S   K   P   P   D   E   I   K   Q   S   G      20
CT  AATGATGATAAGTTATATCGGGCAGATTCTAGACCTCCTGATGAAATAAAGCAGTCAGGT

LT  AGTCTTATGCCCAGAGGT...AATGAGTACTTCGATAGAGGAACTCAAATGAATATTAAT
     S   L   M   P   R   G   Q   N   E   Y   F   D   R   G   T   Q   M   N   I   N      39
    ------------------------------------------------------------
     G   L   M   P   R   G   Q   S   E   Y   F   D   R   G   T   Q   M   N   I   N      40
CT  GGTCTTATGCCAAGAGGACAGAGTGAGTACTTTGACCGAGGTACTCAAATGAATATCAAC

LT  CTTTATGATCACGCGAGAGGAACACAAACCGGCTTTGTCAGATATGATGACGGATATGTT
     L   Y   D   H   A   R   G   T   Q   T   G   F   V   R   Y   D   D   G   Y   V      59
    ------------------------------------------------------------
     L   Y   D   H   A   R   G   T   Q   T   G   F   V   R   H   D   D   G   Y   V      60
CT  CTTTATGATCATGCAAGAGGAACTCAGACGGGATTTGTTAGGCACGATGATGGATATGTT

LT  TCCACTTCTCTTAGTTTGAGAAGTGCTCACTTAGCAGGACAGTATATATTATCAGGATAT
     S   T   S   L   S   L   R   S   A   H   L   A   G   Q   Y   I   L   S   G   Y      79
    ------------------------------------------------------------
     S   T   S   I   S   L   R   S   A   H   L   V   G   Q   T   I   L   S   G   H      80
CT  TCCACCTCAATTAGTTTGAGAAGTGCCCACTTAGTGGGTCAAACTATATTGTCTGGTCAT

LT  TCACTTACTATATATATCGTTATAGCA.........AATATGTTTAATGTTAATGATGTA
     S   L   T   I   Y   I   V   I   A               N   M   F   N   V   N   D   V      96
    ------------------------------------------------------------
     S   T   Y   Y   I   Y   V   I   A   T   A   P   N   M   F   N   V   N   D   V     100
CT  TCTACTTATTATATATATGTTATAGCCACTGCACCCAACATGTTTAACGTTAATGATGTA

LT  ATTAGCGTATACAGCCCTCACCCATATGAACAGGAGGTTTCTGCGTTAGGTGGAATACCA
     I   S   V   Y   S   P   H   P   Y   E   Q   E   V   S   A   L   G   G   I   P     116
    ------------------------------------------------------------
     L   G   A   Y   S   P   H   P   D   E   Q   E   V   S   A   L   G   G   I   P     120
CT  TTAGGGGCATACAGTCCTCATCCAGATGAACAAGAAGTTTCTGCTTTAGGTGGGATTCCA

LT  TATTCTCAGATATATGGATGGTATCGTGTTAATTTTGGTGTGATTGATGAACGATTACAT
     Y   S   Q   I   Y   G   W   Y   R   V   N   F   G   V   I   D   E   R   L   H     136
    ------------------------------------------------------------
     Y   S   Q   I   Y   G   W   Y   R   V   H   F   G   V   L   D   E   Q   L   H     140
CT  TACTCCCAAATATATGGATGGTATCGAGTTCATTTTGGGGTGCTTGATGAACAATTACAT

LT  CGTAACAGGGAATATAGAGACCGGTATTACAGAAATCTGAATATAGCTCCGGCAGAGGAT
     R   N   R   E   Y   R   D   R   Y   Y   R   N   L   N   I   A   P   A   E   D     156
    ------------------------------------------------------------
     R   N   R   G   Y   R   D   R   Y   Y   S   N   L   D   I   A   P   A   A   D     160
CT  CGTAATAGGGGCTACAGAGATAGATATTACAGTAACTTAGATATTGCTCCAGCAGCAGAT
```

FIG. 1A

```
LT    GGTTACAGATTAGCAGGTTTCCCACCGGATCACCAAGCTTGGAGAGAAGAACCCTGGATT
       G  Y  R  L  A  G  F  P  P  D  H  Q  A  W  R  E  E  P  W  I     176
       ------------------------------------------------------------
       G  Y  G  L  A  G  F  P  P  E  H  R  A  W  R  E  E  P  W  I     180
CT    GGTTATGGATTGGCAGGTTTCCCTCCGGAGCATAGAGCTTGGAGGGAAGAGCCGTGGATT

LT    CATCATGCACCACAAGGTTGTGGAGATTCATCAAGAACAATCACAGGTGATACTTGTAAT
       H  H  A  P  Q  G  C  G  D  S  S  R  T  I  T  G  D  T  C  N     196
       ------------------------------------------------------------
       H  H  A  P  P  G  C  G  N  A  P  R  S  S  I  S  N  T  C  D     200
CT    CATCATGCACCGCCGGGTTGTGGGAATGCTCCAAGATCATCGATCAGTAATACTTGCGAT

LT    GAGGAGACCCAGAATCTGAGCACAATATATCTCAGGGAATATCAATCAAAAGTTAAGAGG
       E  E  T  Q  N  L  S  T  I  Y  L  R  E  Y  Q  S  K  V  K  R     216
       ------------------------------------------------------------
       E  K  T  Q  S  L  G  V  K  F  L  D  E  Y  Q  S  K  V  K  R     220
CT    GAAAAAACCCAAAGTCTAGGTGTAAAATTCCTTGACGAATACCAATCTAAAGTTAAAAGA

LT    CAGATATTTTCAGACTATCAGTCAGAGGTTGACATATATAACAGAATTCGGGATGAATTATGA
       Q  I  F  S  D  Y  Q  S  E  V  D  I  Y  N  R  I  R  D  E  L  *
       ----------------------------------------------------------------
       Q  I  F  S  G  Y  Q  S  D  I  D  T  H  N  R  I  K  D  E  L  *
CT    CAAATATTTTCAGGCTATCAATCTGATATTGATACACATAATAGAATTAAGGATGAATTATGA
```

FIG. 1B

FIG. 2

DETOXIFIED MUTANTS OF BACTERIAL
ADP-RIBOSYLATING TOXINS AS
PARENTERAL ADJUVANTS

CROSS-REFERENCE TO RELATED
APPLICATION

This application is a continuation of U.S. patent application Ser. No. 09/044,696, filed Mar. 18, 1998, now U.S. Pat. No. 6,818,222, issued Nov. 16, 2004, from which application priority is claimed pursuant to 35 U.S.C. § 120, and which claims benefit under 35 U.S.C. § 119(e) of provisional application 60/041,227, filed Mar. 21, 1997, all of which applications are incorporated herein by reference in their entireties.

FIELD OF THE INVENTION

The present invention relates to adjuvants useful for the administration of antigens to organisms. In particular, the adjuvants of the invention allow the parenteral delivery of vaccines to raise an immune response.

BACKGROUND OF THE INVENTION

Advances in recombinant DNA technology have made possible the generation of a variety of vaccines, such as subunit vaccines and DNA-based vaccines. These are in addition to the more traditional killed or attenuated vaccines. Adjuvants that enhance the immune system's response to antigenic material are known; however, currently, few adjuvants are approved for human usage, although additional adjuvants are in pre-clinical and clinical studies.

The ADP-ribosylating bacterial toxins, a group of potent toxins to humans, include diphtheria toxin, pertussis toxin (PT), cholera toxin (CT), the *E. coli* heat-labile toxins (LT1 and LT2), *Pseudomonas* endotoxin A, *C. botulinum* C2 and C3 toxins, as well as toxins from *C. perfringens*, *C. spiriforma* and *C. difficile*. These toxins are composed of a monomeric, enzymatically active A subunit which is responsible for ADP-ribosylation of GTP-binding proteins, and a non-toxic B subunit which binds receptors on the surface of the target cell and delivers the A subunit across the cell membrane.

In the case of CT and LT, the A subunit is known to increase intracellular cAMP levels in target cells, while the B subunit is pentameric and binds to GM1 ganglioside receptors. (LT-B also binds additional receptors.)

Previously, observations were made demonstrating that CT is able to induce mucosal and systemic immunity against itself when administered intraduodenally (i.e. to a mucosal surface). The membrane-binding function of CT was shown to be essential for mucosal immunogenicity, but cholera toxoid, also known as the B subunit of CT (CT-B) was inactive in isolation (Pierce and Gowans, *J. Exp. Med.* 1975; 142: 1550; Pierce, *J. Exp Med.* 1978; 148: 195–206).

Subsequently, it was demonstrated that native CT induced immunity to co-administered antigens (Elson, *Curr. Top. Microbiol. Immunol.*, 1989; 146:29; Elson and Ealding, *J. Immunol.* 1984; 133:2892–2897; Elson and Ealding, Ibid. 1984; 132:2736–2741; Elson et al., *J. Immunol. Meth.* 1984; 67:101–118; Lycke and Homgren, *Immunology* 1986; 59:301–339) and that immune responses may be elicted to diptheria or tetanus toxoids when these antigens are applied to skin in combination with CT.

Two approaches have been taken in order to address the problem of CT toxicity. The first approach has involved the use of CT-B as a mucosal adjuvant. CT-B is entirely non-toxic. An adjuvant effect for co-administered CT-B has been alleged in a number of publications (Tamura et al., *J. Immunol.* 1992; 149:981–988; Hirabayashi et al., *Immunology* 1992; 75: 493–498; Gizurarson et al., *Vaccine* 1991; 9:825–832; Kikuta et al., *Vaccine* 1970; 8:595–599; Hirabayashi et al. Ibid. 1990; 8:243–248; Tamura et al., Ibid. 1989; 7:314–32-; Tamura et al., Ibid. 1989; 7:257–262; Tamura et al., Ibid. 1988; 6:409–413; Hirabayashi et al., *Immunology* 1991; 72:329–335 Tamura et al., *Vaccine* 1989; 7:503–505).

However, a number of aspects of the observations reported above were not entirely convincing. For example, it was noted that the adjuvant effect ascribed to CT-B was not H-2 (MHC) restricted. It is known, however, that the immune response to CTB is H-2 (MHC) restricted (Elson and Ealding, *Eur. J. Immuno.* 1987; 17:425–428). Moreover, the alleged adjuvant effect was observed even in individuals already immune to CT-B.

Other groups were unable to observe any mucosal adjuvant effect attributable to CT-B (Lycke and Holmgren, *Immunology* 1986; 59:301–308; Lycke et al., *Eur. J. Immunol.* 1992: 22:2277–2281). Experiments with recombinant CT-B (Holmgren et al., *Vaccine* 1993; 11:1179–1183) confirmed that the alleged effect is largely, if not exclusively, attributable to low levels of contamination of CT-B preparations with CT.

A second approach to eliminating the toxicity of CT has been to mutate the active holotoxin in order to reduce or eliminate its toxicity. The toxicity of CT resides in the A subunit and a number of mutants to CT and its homologue, LT, comprising point mutations in the A subunit, are known in the art. See, for example, International Patent Application WO92/19265. It is accepted in the art that CT and LT are generally interchangeable, showing considerable homology. ADP-ribosylating bacterial toxin mutants have been shown to act as mucosal adjuvants, see International Patent Application WO95/17211.

SUMMARY OF THE INVENTION

Accordingly, there remains a need for an active adjuvant which may be used to increase the immunogenicity of an antigen when administered parenterally, such as intramuscularly, subcutaneously, intravenously, transcutaneously or intradermally. The present invention provides for such parenteral adjuvants in the form of non-toxic ADP ribosylating bacterial toxins. It is demonstrated herein that such mutants, lacking toxicity, are active as parenteral adjuvants and produce high antibody titers and/or induction of cytotoxic T-lymphocytes (CTLs).

In one embodiment, then, the subject invention is directed to a parenteral adjuvant composition comprising a detoxified mutant of a bacterial ADP-ribosylating toxin as the parenteral adjuvant and at least one selected antigen.

In another embodiment, the invention is directed to a parenteral adjuvant composition comprising a detoxified mutant of a bacterial ADP-ribosylating toxin as the parenteral adjuvant and a pharmaceutically acceptable topical vehicle.

In yet another embodiment, the invention is directed to a parenteral adjuvant composition comprising a detoxified mutant of a bacterial ADP-ribosylating toxin as the parenteral adjuvant, a pharmaceutically acceptable topical vehicle and at least one selected antigen.

In another embodiment, the invention is directed to a method for making a parenteral adjuvant composition comprising combining a detoxified mutant of a bacterial ADP-ribosylating toxin as the parenteral adjuvant with at least one selected antigen.

In still a further embodiment, the invention is directed to a method of making a parenteral adjuvant composition comprising combining a detoxified mutant of a bacterial ADP-ribosylating toxin as the parenteral adjuvant with a pharmaceutically acceptable topical vehicle.

In another embodiment, the invention is directed to a method for immunizing a vertebrate subject comprising parenterally administering to the vertebrate subject an immunologically effective amount of a) an adjuvant comprising a detoxified mutant of a bacterial ADP-ribosylating toxin in combination with a pharmaceutically acceptable vehicle; and b) at least one selected antigen.

In particularly preferred embodiments, the non-toxic adjuvant is a detoxified mutant selected from the group consisting of cholera toxin (CT), pertussis toxin (PT), and an *E. coli* heat-labile toxin (LT), particularly LT-K63, LT-R72, CT-S109, and PT-K9/G129.

These and other embodiments of the present invention will readily occur to those of ordinary skill in the art in view of the disclosure herein.

BRIEF DESCRIPTION OF THE FIGURES

FIGS. 1A–1B show the DNA and corresponding amino acid sequences of a wild-type subunit A from an *E. coli* heat labile toxin (LT) (SEQ ID NOS:1 and 2) and a cholera toxin (CT) (SEQ ID NOS:3 and 4).

FIG. 2 shows the serum anti-LT antibody response following transcutaneous administration of representative adjuvant compositions of the present invention. Circles indicate titers from individual mice. If less than five circles are visible per group, two or more values were identical and circles were superimposed. Full triangles indicate mean titers per group ± standard deviation.

DETAILED DESCRIPTION OF THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), METHODS IN ENZYMOLOGY Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

The following amino acid abbreviations are used throughout the text:

| | | | |
|---|---|---|---|
| Alanine (Ala) | A | Arginine (Arg) | R |
| Asparagine (Asn) | N | Aspartic acid (Asp) | D |
| Cysteine (Cys) | C | Glutamine (Gln) | Q |
| Glutamic acid (Glu) | E | Glycine (Gly) | G |
| Histidine (His) | H | Isoleucine (Ile) | I |
| Leucine (Leu) | L | Lysine (Lys) | K |
| Methionine Met) | M | Phenylalanine (Phe) | F |
| Proline (Pro) | P | Serine (Ser) | S |
| Threonine (Thr) | T | Tryptophan (Trp) | W |
| Tyrosine (Tyr) | Y | Valine (Val) | V |

I. Definitions

In describing the present invention, the following terms will be employed, and are intended to be defined as indicated below.

By "parenteral" is meant introduction into the body outside of the digestive tract, such as by subcutaneous, intramuscular, transcutaneous, intradermal, or intravenous administration. This is to be contrasted with adjuvants that are delivered to a mucosal surface, such as oral, intranasal, vaginal, or rectal.

As used herein, "detoxified" refers to both completely nontoxic and low residual toxic mutants of the toxin in question. Preferably, the detoxified protein retains a toxicity of less than 0.01% of the naturally occurring toxin counterpart, more preferably less than 0.001% and even more preferable, less than 0.0001% of the toxicity of the naturally occurring toxin counterpart. The toxicity may be measured in mouse CHO cells or preferably by evaluation of the morphological changes induced in Y1 cells. In particular, Y1 cells are adrenal tumor epithelial cells which become markedly more rounded when treated with a solution containing CT or LT (Ysamure et al., *Cancer Res.* (1966) 26:529–535). The toxicity of CT and LT is correlated with this morphological transition. Thus, the mutant toxins may be incubated with Y1 cells and the morphological changes of the cells assessed.

The term "toxoid" as used herein means a genetically detoxified toxin.

By "antigen" is meant a molecule which contains one or more epitopes (either linear, conformational or both) that will stimulate a host's immune system to make a cellular antigen-specific immune response when the antigen is produced, or a humoral antibody response. Such epitopes may include from about 3 to about 20 or more amino acids. Normally, a B cell epitope will include at least about 5 amino acids but can be as small as 3–4 amino acids. A T cell epitope, such as a CTL epitope, will include at least about 7–9 amino acids, and a helper T cell epitope at least about 12–20 amino acids. The term denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein.

For purposes of the present invention, antigens can be derived from any of several known viruses, bacteria, parasites and fungi. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. T cells can be divided into two major groups called $CD8^+$ T or $CD4^+$ T cells based on expression of either the CD8 or CD4 protein on their surface. $CD8^+$ T cells are often referred to as cytotoxic T cells (CTL) and $CD4^+$ T cells are often called helper T cells (Th). The Th cells can be further divided into Th1 and Th2 cells. In contrast to the B cells, T cells are not capable of recognizing native antigen but require specific processing of such antigens. Fragments of the antigen are presented by antigen presenting cells (APCs) to T cells. These fragments are associated with a specific protein on the surface of the APC. $CD8^+$ T cells recognize the fragment presented by MHC I protein whereas $CD4^+$ T cells recognize antigenic fragments presented by MHC II proteins.

One important aspect of cellular immunity involves an antigen-specific response by CTLs. CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T cells. Helper T cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T cells and/or other white blood cells, including those derived from CD4+ and CD8+ T cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. For a general overview of the immune system and immunological mechanisms see for example: Janeway, C. A. and Travers, P., IMMUNOBIOLOGY, 2nd ed. 1996, Current Biology Ltd./Garland Publishing, New York, N.Y.

A composition which contains a selected antigen along with a detoxified mutant of a bacterial ADP-ribosylating toxin of the present invention, or a vaccine composition which is coadministered with the subject adjuvant, displays "enhanced immunogenicity" when it possesses a greater capacity to elicit an immune response than the immune response elicited by an equivalent amount of the antigen administered without the adjuvant. Thus, a vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the adjuvant composition and antigen controls to animals and comparing antibody titers and/or cellular-mediated immunity against the two using standard assays such as radioimmunoassay, ELISAs, CTL assays, and the like, well known in the art.

For purposes of the present invention, an "effective amount" of an adjuvant will be that amount which enhances an immunological response to a coadministered antigen.

As used herein, "treatment" refers to any of (i) prevention of infection or reinfection, as in a traditional vaccine, (ii) reduction or elimination of symptoms, and (iii) reduction or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like; and fish. The term does not denote a particular age. Thus, both adult and newborn individuals are intended to be covered. The system described above is intended for use in any of the above vertebrate species, since the immune systems of all of these vertebrates operate similarly.

II. Modes of Carrying Out the Invention

The present invention is based on the surprising and unexpected discovery that detoxified mutants of bacterial ADP-ribosylating toxins, such as CT, LT and PT, are able to serve as parenteral adjuvants to enhance humoral and/or cell-mediated immune responses in a vertebrate subject when the adjuvants are administered with a selected antigen. Since the present adjuvants function when administered parenterally, they permit a convenient method of conferring immunity to substances that are not amenable to other modes of administration. Accordingly, the present system is useful with a wide variety of antigens and provides a powerful tool to prevent and/or treat a large number of infections.

Regarding the present invention, any detoxified mutant of a bacterial ADP-ribosylating toxin can be used as a parenteral adjuvant. Such mutants optionally comprise one or more amino acid additions, deletions or substitutions that result in a molecule having reduced toxicity while retaining adjuvanticity. If an amino acid is substituted for the wild-type amino acid, such substitutions may be with a naturally occurring amino acid or may be with a modified or synthetic amino acid. Substitutions which alter the amphotericity and hydrophilicity while retaining the steric effect of the substituting amino acid as far as possible are generally preferred.

The mutants of the invention are preferably in the form of a holotoxin, comprising the mutated A subunit and the B subunit, which may be oligomeric, as in the wild-type holotoxin. The B subunit is preferably not mutated. However, it is envisaged that a mutated A subunit may be used in isolation from the B subunit, either in an essentially pure form or complexed with other agents, which may replace the B subunit and/or its functional contribution.

As explained above, in addition to the completely non-toxic ADP-ribosylating bacterial toxins, toxins can be used wherein a residual toxicity greater than 100 to 10,000 fold lower, or more, than its naturally occurring counterparts is found.

Particularly suitable are detoxified mutants of diphtheria toxin, CT, LT, or PT; such mutations are known in the art. For example, particular mutant LTs in accordance with the invention may possess the following mutations of the A subunit: a Val to Asp, Glu or Tyr substitution at position 53; a Ser to Lys substitution at position 63 (termed LT-K63 herein); an Ala to Arg substitution at position 72 (termed LT-R72 herein); a Val to Lys or Tyr substitution at position 97; a Tyr to Lys, Asp or Ser substitution at position 104; a Pro to Ser substitution at position 106; an Arg to Gly substitution at position 192.

Figure 1B:
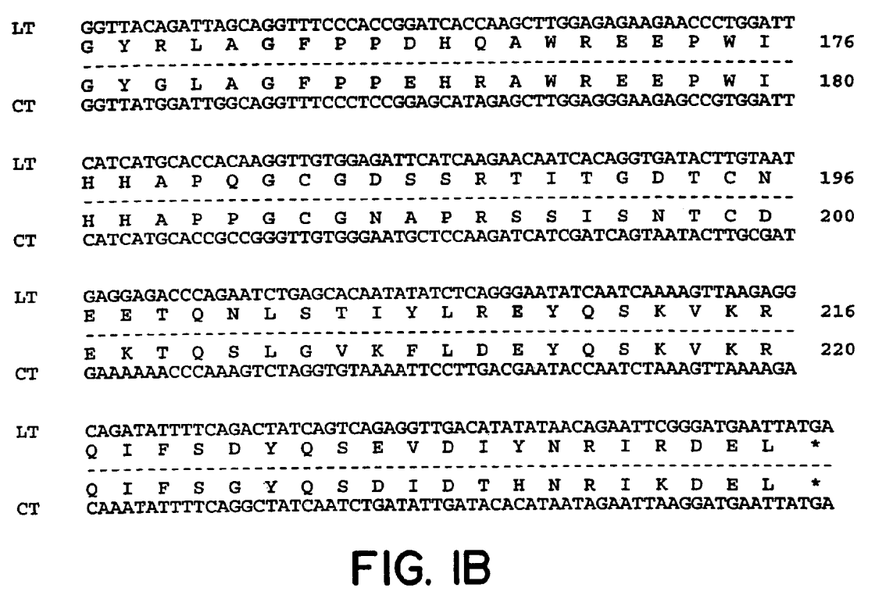

Since the amino acid sequences of CT-A and LT-A are substantially conserved (see FIGS. 1A–1B, (SEQ ID NOS: 1–4)), the changes described above with respect to LT can also be made to the corresponding positions in CT. A particularly preferred CT mutant comprises a substitution of Ser at position 109 (termed CT-S109 herein).

A preferred detoxified mutant of *Bordetella pertussis* is a double mutant where Lys replaces Arg at amino acid position 9 and Gly replaces Glu at amino acid position 129 (termed PT-K9/G129 herein). Many other suitable pertussis toxin (PT) mutants are known in the art.

Methods for the design and production of mutants of CT and/or LT are known in the art. Suitable methods are described in International Patent application W093/13202, as well as W092/19265. In particular, such mutant toxins may be synthesized chemically, using conventional peptide synthesis techniques. See, e.g., See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Alternatively, and preferably, mutations can be made to the wild-type sequence using conventional recombinant techniques such as by preparing synthetic oligonucleotides including the mutations and inserting the mutated sequence into the gene encoding the wild-type protein using restriction endonuclease digestion. (See, e.g., Kunkel, T. A. *Proc. Natl. Acad. Sci. USA* (1985) 82:448; Geisselsoder et al. BioTechniques (1987) 5:786.) Alternatively, the mutations can be effected using a mismatched primer which hybridizes to the wild-type nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409. PCR mutagenesis will also find use for effecting the desired mutations.

The adjuvant of the invention is preferably administered in admixture with at least one antigen against which it is desired to raise an immune response. If the antigen and the adjuvant are not in admixture, it is preferred that they be administered within a relatively short time of each other, at the same site of administration, although there may be a delay of up to 5 days and a two-injection site regime. Thus, the adjuvant may be administered prior or subsequent to, or concurrent with the selected antigen. It has been observed that the adjuvant effect provided by wild-type CT is short-lived (see Lycke and Homgren, *Immunology* 1986: 59: 301–308).

In an alternative embodiment, the adjuvant of the present invention may be administered, optionally in isolation from other antigens, as a boost following systemic or mucosal administration of a vaccine.

Diseases against which the subject may be immunized include all diseases capable of being treated or prevented by immunization, including viral diseases, allergic manifestations, diseases caused by bacterial or other pathogens, such as parasitic organisms, AIDS, autoimmune diseases such as Systemic Lupus Erythematosus, Alzheimer's disease and cancers. Vaccine formulations suitable for delivery may be prepared as set out hereinbelow, while further formulations will be apparent to those of still in the art.

Thus, the antigen may be any antigen to which it is desired to raise an immune response in the subject. Suitable antigens comprise bacterial, viral, fungal and protozoan antigens derived from pathogenic organisms, as well as allergens, and antigens derived from tumors and self-antigens. Typically, the antigen will be a protein, polypeptide or peptide antigen, but alternative antigenic structures, such as nucleic acid antigens, carbohydrate antigens and whole or attenuated or inactivated organisms such as bacteria, viruses or protozoa are included.

Specific examples of antigens useful in the present invention include a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

The adjuvant compositions of the present invention can also be used to deliver antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). By way of example, the viral sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI). (See, Houghton et al., *Hepa-* tology (1991) 14:381–388, for a discussion of HCV proteins, including E1 and E2.) The sequences of these proteins, as well as antigenic fragments thereof, will find use in the present methods. Similarly, the sequence for the δ-antigen from HDV is known (see, e.g., U.S. Pat. No. 5,378,814) and this antigen can also be conveniently used in the present methods.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C., etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immundeficiency virus (SIV) among others. See, e.g. *Virology*, 3rd Edition (W. K. Joklik ed. 1988); *Fundamental Virology*, 2nd Edition (B. N. Fields and D. M. Knipe, eds. 1991), for a description of these and other viruses.

For example, the present adjuvants can be used in conjunction with the gp120 envelope protein from $HIV_{SF2}$, $HIV-1_{CM235}$, $HIV-1_{US4}$, $HIV-1_{IIIB}$ and $HIV-1_{LAI}$. The gp120 sequences for these and a multitude of additional HIV-1 and HIV-2 isolates, including members of the various genetic subtypes of HIV, are known and reported (see, e.g., Myers et al., Los Alamos Database, Los Alamos National Laboratory, Los Alamos, N.Mex. (1992); Myers et al., *Human Retroviruses and Aids*, 1990, Los Alamos, N. Mex.: Los Alamos National Laboratory; and Modrow et al., *J. Virol.* (1987) 61:570–578, for a comparison of the envelope sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

Additionally, the envelope glycoproteins HA and NA of influenza A are of particular interest for generating an immune response. Numerous HA subtypes of influenza A have been identified (Kawaoka et al., *Virology* (1990) 179: 759–767; Webster et al., "Antigenic variation among type A influenza viruses," p. 127–168. In: P. Palese and D. W. Kingsbury (ed.), *Genetics of influenza viruses*. Springer-Verlag, New York). Thus, proteins derived from any of these isolates can also be used in the techniques described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis*, *Neisseria meningitides* (A, B, C, Y), *Hemophilus influenza* type B (HIB), and *Helicobacter pylori*. Examples of parasitic antigens include those derived from organisms causing malaria and Lyme disease.

Furthermore, the methods and compositions described herein provide a means for treating a variety of malignant cancers. For example, the system of the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used prophylactically (to prevent disease) or therapeutically (to treat disease after infection) for a wide variety of diseases. Not only are the compositions herein useful for preventing or treating disease, the subject compositions may also be used to prepare antibodies, both polyclonal and monoclonal, useful for, e.g., diagnostic purposes, as well as for immunopurification of particular antigens against which they are directed.

If polyclonal antibodies are desired, a selected mammal, (e.g., mouse, rabbit, goat, horse, etc.) is immunized with the adjuvant compositions of the present invention, along with the desired antigen. In order to enhance immunogenicity, the antigen can be linked to a carrier prior to immunization. Immunization for the production of antibodies is generally performed by injecting the composition parenterally (generally subcutaneously or intramuscularly). The animal is usually boosted 2–6 weeks later with one or more injections of the antigen, with the adjuvant compositions described herein or with alternate adjuvants. Antibodies may also be generated by in vitro immunization, using methods known in the art. Polyclonal antisera is then obtained from the immunized animal and treated according to known procedures. See, e.g., Jurgens et al. (1985) *J. Chrom.* 348: 363–370.

Monoclonal antibodies are generally prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the protein antigen. B cells, expressing membrane-bound immunoglobulin specific for the antigen, will bind to the plate, and are not rinsed away with the rest of the suspension. Resulting B cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice). See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the hormone of interest, or fragment thereof, can be screened for various properties; i.e., for isotype, epitope, affinity, etc.

Compositions according to the invention may comprise one or more antigens. Furthermore, one or more "pharmaceutically acceptable excipients or vehicles" are present, such as water, saline, glycerol, polyethyleneglycol, hyaluronic acid, ethanol, etc. Additionally, auxiliary substances, such as wetting or emulsifying agents, pH buffering substances, and the like, may be present in such vehicles.

A carrier is optionally present that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as further immunostimulating agents ("adjuvants").

Typically, the compositions are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. Furthermore, compositions suitable for topical use may also be formulated. For example, the adjuvant compositions may be provided in the form of pharmaceutically acceptable topical vehicles such as ointments, creams, gels and emulsions. Ointments, creams and emulsions containing the adjuvants can be prepared using known techniques. A variety of suitable pharmaceutical ointment bases are generally known, including oleaginous bases, anhydrous absorption bases, and oil-in-water (o/w) bases. Oleaginous bases include petrolatum or petrolatum modified by waxes (e.g., liquid petrolatum gelled by the addition of a polyethylene) and those prepared from vegetable fixed oils or animal fats (e.g., lard, benzoinated lard, olive oil, cottonseed oil, or the like). Anhydrous bases include hydrophilic petrolatum, anhydrous lanolin and lanolin derivatives. Oil-in-water bases (e.g., emulsion bases or creams) generally include three parts, the oil phase, the emulsifier and the aqueous phase. The adjuvant, and optionally the antigen, can be included in any one of the phases, or added to the formed emulsion. The oil phase is typically comprised of petrolatum with one or more higher molecular weight alcohols such as cetyl or steryl alcohol. The aqueous phase generally contains preservatives, the water-soluble components of the emulsion system, humectants (such as glycerin, propylene glycol or a polyethylene glycol), as well as optional stabilizers, antioxidants, buffers and the like.

The above pharmaceutical ointments are formed by dispersing finely divided or dissolved adjuvant and, optionally one or more selected antigens, uniformly throughout the vehicle or base. Creams, lotions and emulsions can be formed by way of a two-phase heat system, wherein oil-phase ingredients are combined under heat to provide a liquified, uniform system. The aqueous-phase ingredients are separately combined using heat. The oil and aqueous phases are then added together with constant agitation and allowed to cool. At this point, concentrated agents may be added as a slurry. Volatile or aromatic materials can be added after the emulsion has sufficiently cooled. Preparation of such pharmaceutical compositions is within the general skill of the art. See, e.g., *Remington's Pharmaceutical Sciences*, Mack Publishing Company, Easton, Pa., 18th edition, 1990.

The adjuvants can also be incorporated into gel formulations using a two-phase gel system. Such systems generally comprise a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents for use herein include synthetic macromolecules (e.g., Carbomers®, polyvinyl alcohols and polyoxyethylene-polyoxypropylene copolymers), gums such as tragacanth, as well as sodium alginate, gelatin, methylcellulose, sodium carboxymethylcellulose, methylhydroxyethyl cellulose and hydroxyethyl cellulose. In order to prepare a uniform gel, dispersing agents such as alcohol or glycerin can be added, or the gelling agent can be dispersed by trituration, mechanical mixing or stirring, or combinations thereof.

Lotion preparations are generally liquid or semiliquid preparations containing the adjuvant and, optionally, one or more selected antigens, in a suitable vehicle. Lotions are formed by suspending finely divided solids in an aqueous medium. Optional dispersing agents can be employed to aid in the preparation of the liquid formulation, as well as one or more surface-active agents.

In the cream and ointment formulations described hereinabove, optional ingredients can include materials such as antioxidants, viscosity modifiers (e.g., paraffin wax or lanolin wax), and topical absorption rate modifiers. Actual methods of preparing any of the above formulations are known, or will be apparent, to those skilled in the art. See, e.g., *Remington's Pharmaceutical Sciences*, Mack Publishing Company, Easton, Pa., 18th edition, 1990.

Immunogenic compositions used as vaccines comprise an immunologically effective amount of the adjuvant and an antigen, as well as any other the above-mentioned components, as needed. By "immunologically effective amount", is meant that the administration of that amount to an individual, either in a single dose or as part of a series, is such that an immune response can be generated in the subject to which it is administered. The exact amount necessary will vary depending on the subject being treated; the age and general condition of the subject to be treated; the capacity of the subject's immune system to synthesize antibodies and/or mount a cell-mediated immune response; the degree of protection desired; the severity of the condition being treated; the particular antigen selected and its mode of administration, among other factors. An appropriate effective amount can be readily determined by one of skill in the art. Thus, an "immunologically effective amount" will fall in a relatively broad range that can be determined through routine trials. In general, an "immunologically effective" amount of antigen will be an amount on the order of about 0.1 µg to about 1000 µg, more preferably about 1 µg to about 100 µg.

Similarly, the adjuvant will be present in an amount such that the antigen displays "enhanced immunogenicity," as defined above, as compared to administration of the antigen alone, without the adjuvant. Amounts which are effective for eliciting an enhanced immune response can be readily determined by one of skill in the art.

Dosage treatment may be a single dose schedule or a multiple dose schedule. The vaccine may be administered in conjunction with other immunoregulatory agents.

Additional adjuvants can be used to enhance effectiveness; such adjuvants include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% TWEEN 80 polyoxvethylene sorbitan monooleate surfactant, and 0.5% SPAN 85 sorbitan trioleate surfactant (optionally containing various amounts of MTP-PE (see below), although not required) formulated into submicron particles using a microfluidizer such as Model 110Y microfluidizer (Microfluidics Newton, KA), (b) SAF, containing 10% Squaleene, 0.4% TWEEN 80, 5% PLURONIC L121 block polymer surfactant, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59 are preferred. Muramyl peptides include, but are not limited to, N-acetyl-muramyl-L-threonyl-Disoglutamine (thr-MDP), N-acetyl-normuramyl-$^L$-alanyl-$^D$-isoglutamine (nor-MDP), N-acetyl-moramyl-$^L$-alanyl-$^D$-isoglutaminyl-$^L$-alanine-2-(1'-2'-dipalmitoyl-sn-glycero-3-hydroxyphosphoryloxy)-ethylamine (MTP-PE), etc.

The invention further provides a method for the manufacture of an adjuvanted vaccine comprising the steps of:

a) performing site-directed mutagenesis on the A subunit of a bacterial ADP-ribosylating toxin in order to detoxify the toxin; and b) combining the detoxified toxin with an antigen, such that it functions as a parenteral adjuvant.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of LT-K63

LT-K63, for use in the following experiments, was made as follows. Site-directed mutagenesis was used to replace the Ser reside at position 63 of the A subunit of LT with Lys in order to construct a non-toxic LT mutant that would still assemble as a holotoxin with cell binding activity. The mutant protein, named LT-K63, was purified and tested for ADP-ribosyltransferase and toxic activity in several assays. LT-K63 was still able to bind GM1 ganglioside receptor but showed a complete loss of enzymatic activity, in agreement with published data (Lobet et al., *Infect. Immun.* 1991; 59:2870–2879). Further, LT-K63 was inactive in the mouse ileal loop assay and in vitro on Y1 cells.

EXAMPLE 2

Parenteral Adjuvant Activity of LT-K63 with HSV qD2 in Mice

The LT-K63 mutant, produced as described in Example 1, was tested as a parenteral adjuvant with herpes simplex virus type 2 (HSV-2) gD antigen as follows.

a. Mice were immunized twice by intramuscular injection one month apart with a 10 μg dose of the LT-K63 mutant and a 10 μg dose of HSV-2 gD2 antigen. Sera were collected on day 0 and two weeks after the second immunization (day 42). The antibody responses against HSV-2 gD2 were measured by ELISA. The geometric mean titers plus or minus standard error are listed in Table 1. This experiment illustrates the ability of the LT-K63 mutant in combination with HSV-2 gD2 to produce an immune response in mice.

TABLE 1

Serum anti-gD2 titers of mice immunized with LT-K63 and gD2

| Animal # | Day 0 | Day 42 |
|---|---|---|
| BL898 | <10 | 4510 |
| BL899 | <10 | 45920 |
| BL900 | <10 | 7535 |
| BL901 | <10 | 56585 |
| BL902 | <10 | 74085 |
| BL903 | <10 | 8845 |
| BL904 | <10 | 4340 |
| BL905 | <10 | 19430 |
| BL906 | <10 | 6380 |
| BL907 | <10 | 9125 |
| GMT +/− SEM | | 13975 +/− 4726 | b. Mice were immunized twice by intramuscular injection one month apart with 10 μg HSV-2 gD2. Sera were collected on day 0 and two weeks after the second immunization. The antibody responses against HSV-2 gD2 were measured by ELISA and are shown as geometric mean titer plus or minus standard error in Table 2. The 90-fold lower antibody response produced by HSV-2 gD2 (150) compared to HSV-2 gD2 combined with LT-K63 (13980) illustrates the parenteral adjuvant activity of LT-K63 with HSV-2 gD2.

TABLE 2

Serum anti-HSV gD2 antibody titers of mice immunized with gD2

| Animal # | Day 14 Sera | Day 42 Sera |
|---|---|---|
| BC047 | <10 | 348 |
| BC048 | <10 | 11 |
| BC049 | <10 | 17 |
| BC050 | <10 | 222 |
| BC051 | <10 | 73 |
| BC052 | <10 | 44 |
| BC053 | <10 | 2053 |
| BC054 | <10 | 2882 |
| GMT +/− SEM | | 151 +/− 111 |

EXAMPLE 3

Parenteral Adjuvant Activity of LT-K63 with Influenza HA in Mice

Mice were immunized twice by intramuscular injection one month apart with 1 μg LT-K63 (produced as described in Example 1) and 1 μg A/Texas HA (hemagglutinin) antigen or 1 μg A/Texas HA alone. Sera were collected two weeks after the second immunization. The anti-HA ELISA titers are shown as geometric mean titer plus or minus standard error in Table 3. The 11-fold higher antibody response observed in the group receiving HA antigen combined with the LT-K63 mutant (70380) compared with the group receiving HA antigen alone (6390) illustrates the effectiveness of LT-K63 as a parenteral adjuvant with influenza HA antigen.

TABLE 3

Serum anti-HA titers of mice immunized with HA or HA with LT-K63

| HA Animal # | Day 42 | HA + LT-K63 Animal # | Day 42 |
|---|---|---|---|
| CN 622 | 3698 | | |
| CN 623 | 7778 | | |
| CN 624 | 5506 | | |
| CN 625 | 5142 | | |
| CN 626 | 7109 | | |
| CN 627 | 7422 | | |
| CN 628 | 51463 | | |
| CN 629 | 19299 | | |
| CN 630 | 2906 | | |
| CN 631 | 427 | | |
| CN 632 | 2601 | CN 642 | 73486 |
| CN 633 | 4817 | CN 643 | 70019 |
| CN 634 | 7315 | CN 644 | 43773 |
| CN 635 | 19056 | CN 645 | 79454 |
| CN 636 | 19979 | CN 646 | 229580 |
| CN 637 | 2049 | CN 647 | 43157 |
| CN 638 | 3404 | CN 648 | 29928 |
| CN 639 | 12447 | CN 649 | 84437 |
| CN 640 | 4817 | CN 650 | 88956 |
| CN 641 | 16752 | CN 651 | 74790 |
| GMT +/− SEM | 6391 +/− 1484 | | 70378 +/− 12194 |

EXAMPLE 4

Parenteral Adjuvant Activity of LT-K63 with HIV p24 Gag in Mice a. Mice were immunized three times by subcutaneous injection 1 week apart with 10 μg LT-K63 (produced as described in Example 1) and 10 μg HIV p24 gag or 10 μg HIV p24 gag alone. HIV p24 gag-specific CTL activity is depicted in Table 4. CTL activity was measured in a standard chromium release assay and is presented as % specific lysis. In particular, SVBalb (H-2d) and MC57 (H-2b) target cells were incubated with 51Cr and 1 uM p7g peptide for 1 hour. Effector cells (E) were cultured with target cells (T) at various E:T ratios for 4 hours. The average cpm from duplicate wells was used to calculate percent specific 5lCr release. Allogeneic Mc57 target cells and syngeneic SvBalb target cells had low background killing. Syngeneic SvBalb cells pulsed with HIV p24 gag epitope peptide p7g had 69% specific lysis at a 50:1 E:T ratio for HIV p24 gag with LT-K63. In contrast, HIV p24 gag alone induced only 29% killing under the same conditions. The group receiving LT-K63 had a higher CTL response in contrast to the gag alone group. This illustrates the adjuvant activity of LT-K63 for CTL induction with HIV p24 gag.

TABLE 4

CTL Responses of Mice Immunized with HIV gag and LT-K63K

| | | % specific lysis | | |
|---|---|---|---|---|
| | Effector:Target | Mc57/p7g | SvB/p7g | SvB/— |
| LT-K63 + HIV p24 gag | 50:1 | 2 | 69 | 7 |
| | 10 | 3 | 31 | 7 |
| | 2 | 4 | 14 | 4 |
| HIV p24 gag | 50:1 | 5 | 29 | 4 |
| | 10 | 3 | 12 | 2 |
| | 2 | 2 | 5 | 3 | b. Mice were immunized twice by subcutaneous injection one month apart with 10 μg LT-K63 and 10 μg HIV p24 gag. Sera were collected two weeks after the second immunization. The anti-HIV p24 gag titers are shown as geometric mean titer plus or minus standard error in Table 5. This experiment illustrates the ability of LT-K63 in combination with HIV p24 gag to produce an anti-HIV p24 gag response in mice.

TABLE 5

Antibody responses of mice immunized with p24 gag

| Animal # | Day 0 | Day 42 |
|---|---|---|
| CP386 | 13 | 220406 |
| CP387 | 15 | 153674 |
| CP388 | 9 | 235706 |
| CP389 | 20 | 350167 |
| GMT +/− SEM | | 229900 +/− 38800 |

EXAMPLE 5

Transcutaneous Adjuvant Activity of LT-K63 and LT-R72

For the following experiments, the LT wild-type (LTwt), LT-K63 and LT-R72 mutants were obtained as described (Giuliani et al., "Mucosal Adjuvanticity of LTR72, a Novel Mutant of *Escherichia coli* Heat-Labile Enterotoxin with Partial Knock-Out of ADP Ribosyltransferase Activity," *J. Exp. Med.* 187:in press). The antigen used, $CRM_{197}$, is a well-characterized non-toxic diphtheria toxin mutant. See, e.g., Bixler et al. (1989) *Adv. Exp. Med. Biol.* 251:175, Constantino et al. (1992) Vaccine; International Publication No. WO 96/14086.

For transcutaneous immunization, on day 0, groups of 5 female BALB/c mice were anesthetized with an intraperitoneal injection of 100 μl/10 g of weight of a solution of Ketavet™ 50 (20% v/v), Rompun™ (3% v/v), and Combelen™ (3% v/v) in sterile saline. Mice were then shaved on the back (about 2 cm²), and 100 μl of phosphate-buffered saline (PBS) containing 100 μg of CRM197 and 50 μg of LTwt or LT mutants were gently applied on the shaved skin. Mice were kept under anesthesia for about 1 hour, then washed with lukewarm tap water, and dried. The same procedure was repeated on day 21. Third and fourth immunizations were performed on day 51 and day 66, respectively. On the same dates, control groups of 5 mice received CRM197 (10 μg) and LTwt (1 μg) intranasally (20 μl volume).

Serum samples were taken at days −1, 20, 35, 65, and 80. Antibodies to LT and CRM were determined by standard ELISA procedures.

Figure 2:
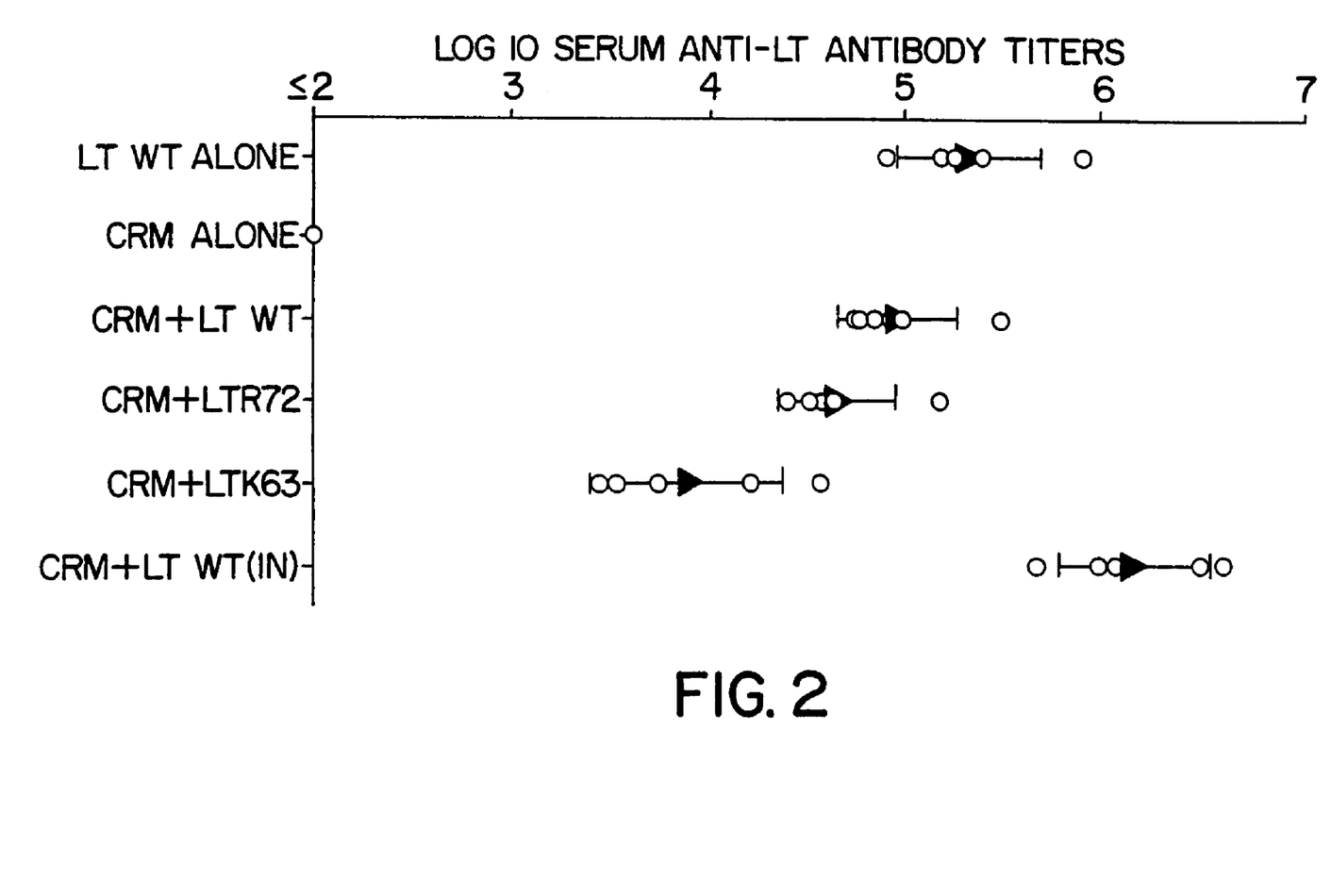

No anti-CRM antibody response was detectable. As shown in Table 6 and FIG. 2, transcutaneous immunization induced a very strong anti-LT antibody response after one immunization (see Table 6), which was boosted after the second immunization (see Table 6 and FIG. 2). Thus, transcutaneous immunization (i.e., application of soluble antigens plus mucosal adjuvants on the skin) induced the production of specific antibodies, showing that the immune system responded to the LT proteins. This result evidences that these proteins may be useful as transcutaneous adjuvants.

TABLE 6

Serum anti-LT antibody titers in BALB/c mice immunized transcutaneously

| | mouse n. | day −1 (preimmune) | day 20 (post-1) | day 35 (post-2) | log titer day 35 | mean | SD |
|---|---|---|---|---|---|---|---|
| Group 1 tc | 1 | *0 | 60856 | 81127 | 4.91 | | |
| LT w.t. | 2 | 0 | 31319 | 833666 | 5.92 | | |
| | 3 | 0 | 109229 | 256225 | 5.41 | 5.34 | 0.37 |
| | 4 | 0 | 129280 | 182907 | 5.26 | | |
| | 5 | 0 | 35628 | 156077 | 5.19 | | |
| Group 2 tc | 6 | 0 | 0 | 0 | | | |
| CRM | 7 | 0 | 0 | 0 | | | |
| | 8 | 0 | 0 | 0 | | | |
| | 9 | 0 | 0 | 0 | | | |
| | 10 | 0 | 0 | 0 | | | |
| Group 3 tc | 11 | 0 | 9593 | 99577 | 5.00 | | |
| CRM + LT | 12 | 0 | 4606 | 73229 | 4.86 | | |
| w.t. | 13 | 0 | 3455 | 60058 | 4.78 | 4.98 | 0.31 |
| | 14 | 0 | 5137 | 56589 | 4.75 | | |
| | 15 | 0 | 20997 | 327216 | 5.51 | | |
| Group 4 tc | 16 | 0 | 7691 | 16501 | 4.22 | | |
| CRM + LTK63 | 17 | 0 | 6307 | 37822 | 4.58 | | |
| | 18 | 0 | 404 | 2770 | 3.44 | 3.90 | 0.49 |
| | 19 | 0 | 572 | 5382 | 3.73 | | |
| | 20 | 0 | 843 | 3278 | 3.52 | | |
| Group 5 tc | 21 | 0 | 2401 | 25676 | 4.41 | | |
| CRM + LTR72 | 22 | 0 | 6868 | 45181 | 4.65 | | |
| | 23 | 0 | 6868 | 33891 | 4.53 | 4.67 | 0.30 |
| | 24 | 0 | 8049 | 38174 | 4.58 | | |
| | 25 | 0 | 19452 | 186017 | 5.19 | | |
| Group 6 | 26 | 0 | 169516 | 1195152 | 6.08 | | |
| i.n. CRM + LT | 27 | 0 | 104288 | 489685 | 5.69 | | |
| w.t. | 28 | 0 | 210832 | 4000000 | 6.60 | 6.17 | 0.37 |
| | 29 | 0 | 187184 | 989957 | 6.00 | | |
| | 30 | 0 | 289546 | 3105000 | 6.49 | | |

*0 = negative (titer < 50)
Groups 1 to 5 were immunized transcutaneously (tc), group 6 intranasally. For tc immunizations (days 0 and 21), groups of BALB/c mice were shaved on the back (about 2 cm$^2$) and kept under anesthesia for 1 hour. During this time, 100 microliters of PBS containing antigen CRM197 (100 micrograms) and LT or LT mutants (50 micrograms) were applied on the shaved skin. Mice were then extensively washed with lukewarm water to avoid possible oralintake of residual antigens. Serum samples were taken at the dates indicated, and tested by ELISA for quantitation of specific antibodies.

Thus, parenteral adjuvants comprising detoxified mutants of a bacterial ADP-ribosylating toxin are disclosed. Although preferred embodiments of the subject invention have been described in some detail, it is understood that obvious variations can be made without departing from the spirit and the scope of the invention as defined by the appended claims.

What is claimed is:

1. The method for immunizing a vertebrate subject against at least one selected antigen, the method comprising the step of parenterally administering to the vertebrate subject an immunologically effective amount of
   a) a parenteral adjuvant comprising a detoxified mutant of an *E. coli* heat-labile (LT) ADP-ribosylating toxin in combination with a pharmaceutically acceptable vehicle, wherein said detoxified mutant is LT-K63; and
   b) at least one selected antigen.

2. The method according to claim 1, wherein the adjuvant and the antigen are administered subcutaneously, transcutaneously or intramuscularly.

3. The method according to claim 1, wherein the pharmaceutically acceptable vehicle is a topical vehicle.

4. The method according to claim 1, wherein the adjuvant and the antigen are administered transcutaneously.

5. The method according to claim 1, wherein the adjuvant is administered to the vertebrate subject prior to administering the selected antigen.

6. The method according to claim 1, wherein the adjuvant is administered to the vertebrate subject subsequent to administering the selected antigen.

7. The method according to claim 1, wherein the antigen is administered to the vertebrate subject concurrent with administering the selected antigen.

8. The method of claim 1, wherein said antigen is a viral antigen.

9. The method of claim 8, wherein said viral antigen is selected from the group consisting of an influenza antigen, a herpes simplex virus (HSV) antigen, a human immunodeficiency virus (HIV) antigen, a cytomegalovirus (CMV) antigen, a hepatitis C virus (HCV) antigen, a delta hepatitis virus (HDV) antigen, a poliovirus antigen, a hepatitis A virus (HAV) antigen, an Epstein-Barr virus (EBV) antigen, a varicella zoster virus (VZV) antigen, and a respiratory syncytial virus (RSV) antigen.

10. The method of claim 9, wherein said viral antigen is an influenza virus antigen.

11. The method of claim 9, wherein said viral antigen is a poliovirus antigen.

12. The method of claim 9, wherein said viral antigen is a RSV antigen.

13. The method of claim 1, wherein said antigen is a bacterial antigen.

14. The method of claim 13, wherein said bacterial antigen is selected from the group consisting of *Bordetella pertussis* antigens, *Helicobacter pylori* antigens, meningococcus A antigens, meningococcus B antigens, and meningococcus C antigens.

15. The method of claim 14, wherein said bacterial antigen is a *Bordetella pertussis* antigen.

16. The method of claim 14, wherein said bacterial antigen is an *Helicobacter pylori* antigen.

17. The method of claim 14, wherein said bacterial antigen is a meningococcus A antigen.

18. The method of claim 14, wherein said bacterial antigen is a meningococcus B antigen.

19. The method of claim 14, wherein said bacterial antigen is a meningococcus C antigen.

* * * * *

SEQUENCE LISTING

```
<160> NUMBER OF SEQ ID NOS: 5

<210> SEQ ID NO 1
<211> LENGTH: 711
<212> TYPE: DNA
<213> ORGANISM: Artificial Sequence
<220> FEATURE:
<221> NAME/KEY: CDS
<222> LOCATION: (1)..(708)
<220> FEATURE:
<223> OTHER INFORMATION: Description of Artificial Sequence: wild-type
      Subunit A from E. coli heat labile toxin

<400> SEQUENCE: 1 aat ggc gac aga tta tac cgt gct gac tct aga ccc cca gat gaa ata       48
Asn Gly Asp Arg Leu Tyr Arg Ala Asp Ser Arg Pro Pro Asp Glu Ile
  1               5                  10                  15 aaa cgt ttc cgg agt ctt atg ccc aga ggt aat gag tac ttc gat aga       96
Lys Arg Phe Arg Ser Leu Met Pro Arg Gly Asn Glu Tyr Phe Asp Arg
```

```
                      20                    25                       30 gga act caa atg aat att aat ctt tat gat cac gcg aga gga aca caa      144
Gly Thr Gln Met Asn Ile Asn Leu Tyr Asp His Ala Arg Gly Thr Gln
            35                  40                  45 acc ggc ttt gtc aga tat gat gac gga tat gtt tcc act tct ctt agt      192
Thr Gly Phe Val Arg Tyr Asp Asp Gly Tyr Val Ser Thr Ser Leu Ser
 50                  55                  60 ttg aga agt gct cac tta gca gga cag tat ata tta tca gga tat tca      240
Leu Arg Ser Ala His Leu Ala Gly Gln Tyr Ile Leu Ser Gly Tyr Ser
 65                  70                  75                  80 ctt act ata tat atc gtt ata gca aat atg ttt aat gtt aat gat gta      288
Leu Thr Ile Tyr Ile Val Ile Ala Asn Met Phe Asn Val Asn Asp Val
                85                  90                  95 att agc gta tac agc cct cac cca tat gaa cag gag gtt tct gcg tta      336
Ile Ser Val Tyr Ser Pro His Pro Tyr Glu Gln Glu Val Ser Ala Leu
            100                 105                 110 ggt gga ata cca tat tct cag ata tat gga tgg tat cgt gtt aat ttt      384
Gly Gly Ile Pro Tyr Ser Gln Ile Tyr Gly Trp Tyr Arg Val Asn Phe
        115                 120                 125 ggt gtg att gat gaa cga tta cat cgt aac agg gaa tat aga gac cgg      432
Gly Val Ile Asp Glu Arg Leu His Arg Asn Arg Glu Tyr Arg Asp Arg
    130                 135                 140 tat tac aga aat ctg aat ata gct ccg gca gag gat ggt tac aga tta      480
Tyr Tyr Arg Asn Leu Asn Ile Ala Pro Ala Glu Asp Gly Tyr Arg Leu
145                 150                 155                 160 gca ggt ttc cca ccg gat cac caa gct tgg aga gaa gaa ccc tgg att      528
Ala Gly Phe Pro Pro Asp His Gln Ala Trp Arg Glu Glu Pro Trp Ile
                165                 170                 175 cat cat gca cca caa ggt tgt gga gat tca tca aga aca atc aca ggt      576
His His Ala Pro Gln Gly Cys Gly Asp Ser Ser Arg Thr Ile Thr Gly
            180                 185                 190 gat act tgt aat gag gag acc cag aat ctg agc aca ata tat ctc agg      624
Asp Thr Cys Asn Glu Glu Thr Gln Asn Leu Ser Thr Ile Tyr Leu Arg
        195                 200                 205 gaa tat caa tca aaa gtt aag agg cag ata ttt tca gac tat cag tca      672
Glu Tyr Gln Ser Lys Val Lys Arg Gln Ile Phe Ser Asp Tyr Gln Ser
    210                 215                 220 gag gtt gac ata tat aac aga att cgg gat gaa tta tga                  711
Glu Val Asp Ile Tyr Asn Arg Ile Arg Asp Glu Leu
225                 230                 235

<210> SEQ ID NO 2
<211> LENGTH: 236
<212> TYPE: PRT
<213> ORGANISM: Artificial Sequence
<220> FEATURE:
<223> OTHER INFORMATION: Description of Artificial Sequence: wild-type
      Subunit A from E. coli heat labile toxin

<400> SEQUENCE: 2

Asn Gly Asp Arg Leu Tyr Arg Ala Asp Ser Arg Pro Pro Asp Glu Ile
  1               5                  10                  15

Lys Arg Phe Arg Ser Leu Met Pro Arg Gly Asn Glu Tyr Phe Asp Arg
            20                  25                  30

Gly Thr Gln Met Asn Ile Asn Leu Tyr Asp His Ala Arg Gly Thr Gln
        35                  40                  45

Thr Gly Phe Val Arg Tyr Asp Asp Gly Tyr Val Ser Thr Ser Leu Ser
    50                  55                  60

Leu Arg Ser Ala His Leu Ala Gly Gln Tyr Ile Leu Ser Gly Tyr Ser
 65                  70                  75                  80
```

```
Leu Thr Ile Tyr Ile Val Ile Ala Asn Met Phe Asn Val Asn Asp Val
                85                  90                  95

Ile Ser Val Tyr Ser Pro His Pro Tyr Glu Gln Glu Val Ser Ala Leu
            100                 105                 110

Gly Gly Ile Pro Tyr Ser Gln Ile Tyr Gly Trp Tyr Arg Val Asn Phe
            115                 120                 125

Gly Val Ile Asp Glu Arg Leu His Arg Asn Arg Glu Tyr Arg Asp Arg
        130                 135                 140

Tyr Tyr Arg Asn Leu Asn Ile Ala Pro Ala Glu Asp Gly Tyr Arg Leu
145                 150                 155                 160

Ala Gly Phe Pro Pro Asp His Gln Ala Trp Arg Glu Glu Pro Trp Ile
                165                 170                 175

His His Ala Pro Gln Gly Cys Gly Asp Ser Ser Arg Thr Ile Thr Gly
            180                 185                 190

Asp Thr Cys Asn Glu Glu Thr Gln Asn Leu Ser Thr Ile Tyr Leu Arg
            195                 200                 205

Glu Tyr Gln Ser Lys Val Lys Arg Gln Ile Phe Ser Asp Tyr Gln Ser
        210                 215                 220

Glu Val Asp Ile Tyr Asn Arg Ile Arg Asp Glu Leu
225                 230                 235

<210> SEQ ID NO 3
<211> LENGTH: 723
<212> TYPE: DNA
<213> ORGANISM: Artificial Sequence
<220> FEATURE:
<221> NAME/KEY: CDS
<222> LOCATION: (1)..(720)
<220> FEATURE:
<223> OTHER INFORMATION: Description of Artificial Sequence: wild-type
      CT subunit A

<400> SEQUENCE: 3 aat gat gat aag tta tat cgg gca gat tct aga cct cct gat gaa ata      48
Asn Asp Asp Lys Leu Tyr Arg Ala Asp Ser Arg Pro Pro Asp Glu Ile
  1               5                  10                  15 aag cag tca ggt ggt ctt atg cca aga gga cag agt gag tac ttt gac       96
Lys Gln Ser Gly Gly Leu Met Pro Arg Gly Gln Ser Glu Tyr Phe Asp
             20                  25                  30 cga ggt act caa atg aat atc aac ctt tat gat cat gca aga gga act      144
Arg Gly Thr Gln Met Asn Ile Asn Leu Tyr Asp His Ala Arg Gly Thr
         35                  40                  45 cag acg gga ttt gtt agg cac gat gat gga tat gtt tcc acc tca att      192
Gln Thr Gly Phe Val Arg His Asp Asp Gly Tyr Val Ser Thr Ser Ile
     50                  55                  60 agt ttg aga agt gcc cac tta gtg ggt caa act ata ttg tct ggt cat      240
Ser Leu Arg Ser Ala His Leu Val Gly Gln Thr Ile Leu Ser Gly His
 65                  70                  75                  80 tct act tat tat ata tat gtt ata gcc act gca ccc aac atg ttt aac      288
Ser Thr Tyr Tyr Ile Tyr Val Ile Ala Thr Ala Pro Asn Met Phe Asn
                 85                  90                  95 gtt aat gat gta tta ggg gca tac agt cct cat cca gat gaa caa gaa      336
Val Asn Asp Val Leu Gly Ala Tyr Ser Pro His Pro Asp Glu Gln Glu
            100                 105                 110 gtt tct gct tta ggt ggg att cca tac tcc caa ata tat gga tgg tat      384
Val Ser Ala Leu Gly Gly Ile Pro Tyr Ser Gln Ile Tyr Gly Trp Tyr
        115                 120                 125 cga gtt cat ttt ggg gtg ctt gat gaa caa tta cat cgt aat agg ggc      432
Arg Val His Phe Gly Val Leu Asp Glu Gln Leu His Arg Asn Arg Gly
```

```
                130                 135                 140
tac aga gat aga tat tac agt aac tta gat att gct cca gca gca gat      480
Tyr Arg Asp Arg Tyr Tyr Ser Asn Leu Asp Ile Ala Pro Ala Ala Asp
145                 150                 155                 160 ggt tat gga ttg gca ggt ttc cct ccg gag cat aga gct tgg agg gaa      528
Gly Tyr Gly Leu Ala Gly Phe Pro Pro Glu His Arg Ala Trp Arg Glu
                165                 170                 175 gag ccg tgg att cat cat gca ccg ccg ggt tgt ggg aat gct cca aga      576
Glu Pro Trp Ile His His Ala Pro Pro Gly Cys Gly Asn Ala Pro Arg
                180                 185                 190 tca tcg atc agt aat act tgc gat gaa aaa acc caa agt cta ggt gta      624
Ser Ser Ile Ser Asn Thr Cys Asp Glu Lys Thr Gln Ser Leu Gly Val
                195                 200                 205 aaa ttc ctt gac gaa tac caa tct aaa gtt aaa aga caa ata ttt tca      672
Lys Phe Leu Asp Glu Tyr Gln Ser Lys Val Lys Arg Gln Ile Phe Ser
210                 215                 220 ggc tat caa tct gat att gat aca cat aat aga att aag gat gaa tta      720
Gly Tyr Gln Ser Asp Ile Asp Thr His Asn Arg Ile Lys Asp Glu Leu
225                 230                 235                 240 tga                                                                  723
```

<210> SEQ ID NO 4
<211> LENGTH: 240
<212> TYPE: PRT
<213> ORGANISM: Artificial Sequence
<220> FEATURE:
<223> OTHER INFORMATION: Description of Artificial Sequence: wild-type
      CT subunit A

<400> SEQUENCE: 4

```
Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser Ser Ile Ser Asn Thr Cys Asp Glu Lys Thr Gln Ser Leu Gly Val
        195                 200                 205

Lys Phe Leu Asp Glu Tyr Gln Ser Lys Val Lys Arg Gln Ile Phe Ser
```

```
                     210                 215                 220
Gly Tyr Gln Ser Asp Ile Asp Thr His Asn Arg Ile Lys Asp Glu Leu
225                 230                 235                 240

<210> SEQ ID NO 5
<211> LENGTH: 240
<212> TYPE: PRT
<213> ORGANISM: Artificial Sequence
<220> FEATURE:
<223> OTHER INFORMATION: Description of Artificial Sequence: wild-type
      Subunit A from E. coli heat labile toxin

<400> SEQUENCE: 5

Asn Gly Asp Arg Leu Tyr Arg Ala Asp Ser Arg Pro Pro Asp Glu Ile
  1               5                  10                  15

Lys Arg Ser Gly Gly Leu Met Pro Arg Gly His Asn Glu Tyr Phe Asp
                 20                  25                  30

Arg Gly Thr Gln Met Asn Ile Asn Leu Tyr Asp His Ala Arg Gly Thr
             35                  40                  45

Gln Thr Gly Phe Val Arg Tyr Asp Asp Gly Tyr Val Ser Thr Ser Leu
 50                  55                  60

Ser Leu Arg Ser Ala His Leu Ala Gly Gln Ser Ile Leu Ser Gly Tyr
 65                  70                  75                  80

Ser Thr Tyr Tyr Ile Tyr Val Ile Ala Thr Ala Pro Asn Met Phe Asn
                 85                  90                  95

Val Asn Asp Val Leu Gly Val Tyr Ser Pro His Pro Tyr Glu Gln Glu
                100                 105                 110

Val Ser Ala Leu Gly Gly Ile Pro Tyr Ser Gln Ile Tyr Gly Trp Tyr
                115                 120                 125

Arg Val Asn Phe Gly Val Ile Asp Glu Arg Leu His Arg Asn Arg Glu
                130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
                180                 185                 190

Thr Ile Thr Gly Asp Thr Cys Asn Glu Glu Thr Gln Asn Leu Ser Thr
                195                 200                 205

Ile Tyr Leu Arg Glu Tyr Gln Ser Lys Val Lys Arg Gln Ile Phe Ser
                210                 215                 220

Asp Tyr Gln Ser Glu Val Asp Ile Tyr Asn Arg Ile Arg Asp Glu Leu
225                 230                 235                 240
```